United States Patent [19]
Nilsson et al.

[11] Patent Number: 6,132,431
[45] Date of Patent: Oct. 17, 2000

[54] DEVICE AND METHOD FOR CORRECTING AND STABILIZING A DEVIATING CURVATURE OF A SPINAL COLUMN

[75] Inventors: Jan-Erik Nilsson, Malmö; Stig Aaro, Linköping, both of Sweden

[73] Assignee: Tresona Instrument AB, Malmo, Sweden

[21] Appl. No.: 09/173,749

[22] Filed: Oct. 16, 1998

Related U.S. Application Data

[63] Continuation of application No. PCT/SE97/00609, Apr. 11, 1997.
[60] Provisional application No. 60/025,289, Sep. 19, 1996.

[30] Foreign Application Priority Data

Apr. 18, 1996 [SE] Sweden ................................. 9601473

[51] Int. Cl.$^7$ ................................................. A61B 17/70
[52] U.S. Cl. ............................................. 606/61; 623/17
[58] Field of Search ........................... 606/61, 71; 623/17

[56] References Cited

U.S. PATENT DOCUMENTS

| | | |
|---|---|---|
| 3,648,691 | 3/1972 | Lumb et al. . |
| 4,448,191 | 5/1984 | Rodnyansky et al. . |
| 5,261,912 | 11/1993 | Frigg .......................................... 606/61 |
| 5,368,594 | 11/1994 | Martin et al. .............................. 606/61 |
| 5,387,212 | 2/1995 | Yuan et al. ................................. 606/61 |
| 5,601,552 | 2/1997 | Cotrel ........................................ 606/61 |
| 5,616,142 | 4/1997 | Yuan et al. ................................. 606/71 |
| 5,662,652 | 9/1997 | Schafer et al. ............................. 606/61 |

FOREIGN PATENT DOCUMENTS

| | | |
|---|---|---|
| 0 558 883 | 9/1993 | European Pat. Off. . |
| 2624720 | 6/1989 | France ..................................... 606/61 |
| 1544409 | 2/1990 | U.S.S.R. . |
| WO 93/20771 | 10/1993 | WIPO . |

OTHER PUBLICATIONS

Abstract No. 90–288362/38 of SU 1544409, "Vertebral corrector—with two rigid fasteners mounted on free end of rode in each pair", Derwent Publications Ltd., London, (Abstract Only), 1990.
The brochure: "Système Colorado pour la colonne", 1995.

*Primary Examiner*—Paul J. Hirsch
*Attorney, Agent, or Firm*—Finnegan, Henderson, Farabow, Garrett & Dunner, L.L.P.

[57] ABSTRACT

A device for correcting and stabilizing a curvature of a spinal column by anterior fusion including at least two brace holders (1–5), each adapted to be arranged against an associated vertebral body (7–11) in the spinal column. The device also includes a securing means (6, 6') for securing the respective brace holders (1–5) on said vertebral body (7–11), and at least one elongate brace (12), which is adapted to extend through and between said brace holders (1–5) along the extent of the spinal column and be locked thereto. The brace (12) is plate-shaped, and the brace holder (1–5) is designed to support the brace (12) in such a manner that a first flat side of the brace (12) faces the abutment surface of the brace holder (1–5) on said vertebral body (7–11), whereby the brace (12) is deformable in only one geometric plane during mounting in the brace holder (1–5) and during correction. In a method for contacting and stabilizing the curvature, the brace (12) is arranged to extend through the brace holders (1–5), such that the brace (12) is deformed to substantially follow the curvature. The brace is locked in at least one first brace holder (1), whereupon the spinal column, vertebra by vertebra, is corrected while the brace (12) is gradually clamped and locked in the brace holders (1–5).

11 Claims, 2 Drawing Sheets

DEVICE AND METHOD FOR CORRECTING AND STABILIZING A DEVIATING CURVATURE OF A SPINAL COLUMN

This application is a continuation of Ser. No. PCT/5E97/00609 filed Apr. 11, 1997, and a provisional application serial No. 60/025,289 filed Sep. 19, 1996.

FIELD OF INVENTION

The present invention relates to a device and a method for correcting and stabilising a deviating curvature of a spinal column, particularly a deviating curvature caused by scoliosis.

MEDICAL BACKGROUND

Scoliosis can be divided into functional and structural scoliosis. In functional scoliosis, the spinal column has a lateral, usually C-shaped, deviation which is located in the lower breast and lumbar part of the back. This type of scoliosis does not cause pathological changes in the spinal column and therefore barely requires medical treatment.

On the other hand, the structural scolioses are characterised by both a lateral deviation of the spinal column and a twisting thereof. The spinal column shows structural changes by the vertebrae and the intermediate discs being wedge-shaped. The twisting of the spinal column causes, in scoliosis in the breast part of the back, a deformation of the rib cage, which can affect the heart and lung function. This is one of the most difficult complications of the structural scolioses. Among further complications, mention can be made of reduced ability to move.

Structural scoliosis is treated either by means of a corset or by surgery. The extent of the scoliosis is usually determined by measuring the angle between the upper end plate of the upper neutral vertebra and the lower end plate of the lower neutral vertebra. Treatment by means of a corset is normally applied if the scoliosis exceeds 30° and exhibits reliable progress. Scolioses exceeding 40–50° in non-grown-up and 50–60° in grown-up individuals are suitable to treat surgically.

The surgical treatment can be carried out by posterior fusion, anterior fusion or a combination of these techniques.

In posterior fusion, the spinal column is uncovered from the back side, whereupon a brace is usually applied to the concave side of the spinal column. The brace is fixed to the spinal column by means of screws or hooks, and the scoliosis is corrected by the entire structure being clamped together by means of a special instrument. The stability of the corrected spinal column can then be improved by attaching to the convex side a so-called compression brace. The braces are then interconnected by means of transverse braces.

In anterior fusion, the spinal column is uncovered from the trunk side, whereupon the front parts of the spinal column are explored from the convex side thereof. As a rule, four to six discs are uncovered, which are then resected. Holders are fixed to the vertebral bodies by means of screws which are fastened in the spongeous bone of the vertebral body. Then a brace is fixed to the holders in such a manner that the spinal column is corrected, compressed and stabilised. Anterior fusion is above all used in certain types of back deformations in the lower breast and lumbar parts, which cannot be taken care of by posterior fusion. Scolioses with great defects in the rear arcs may be involved, such as myelocele, rigid and grave scolioses, such as congenital scolioses, or grave forms of kyphosis.

Posterior and anterior fusions are preferably combined in the cases where the frequency of pseudoosteoarthrosis is high. Such a combined fusion will also be more stable.

The operation time in a combined fusion may often amount to 10–11 h, which is an inconveniently long time from the viewpoint of both the surgeons and the patient.

PRIOR-ART

EP-A-0 558 883 describes a type of device for correcting and stabilising a spinal column by anterior fusion. The device comprises threaded braces of circular cross-section, adjusting nuts and pedicel screws, the heads of which have annular recesses for receiving said braces. The pedicel screws are fixed in suitable vertebral bodies in the spinal column, whereupon the threaded braces are arranged to extend through said screw heads. During this working operation, the adjusting nuts are arranged on the threaded brace between the screw heads and are screwed into engagement with these. By turning an adjusting nut on the threaded brace in relation to the screw head, the surgeon can thus distract or compress the spinal column. The adjusting nut can be secured in the desired position by means of a further nut, which must have been screwed onto the brace together with the adjusting nut.

This prior-art construction suffers from several drawbacks. Owing to the large number of loose parts which as described above are included in the construction, the mounting will be comparatively difficult and time-consuming. Moreover, the surgeon may have difficulty in finding space to perform the working operations for turning the nuts. A further serious drawback is the fact that the brace is completely rigid. As the work proceeds, the extent of the brace must in fact be adapted to the extent of the corrected spinal column. This adaptation takes place by bending the brace by means of a special instrument and of course takes time and requires space. The construction also involves a certain risk that the brace is twisted postoperatively, which results in the returning of the defect. Besides, in its mounted state the construction will project a considerable distance beyond the spinal column, which means that neighbouring blood vessels may be damaged by these projecting parts when the patient begins to move after the operation.

The brochure "Système Colorado pour la colonne" (1995) describes a similar correction device comprising holders and rigid braces of circular cross-section. The holders as well as the braces have no threads. The holders are attached by means of screws in suitable vertebrae along the spinal column, whereupon the brace is arranged to extend through all the holders. The brace is then fixed in a first holder, which is anchored in the lowermost vertebral body of the portion that is to be corrected. Subsequently, the brace is fixed in the next holder while the spinal column is being straightened and compressed to a desirable extent. The procedure is repeated until the intended portion of the spinal column has been straightened, compressed and stabilised.

Apart from consisting of fewer parts, this construction suffers essentially from the same drawbacks as the above-mentioned device, i.e. the rigidity of the braces, time-consuming mounting, a risk of the braces twisting postoperatively, and projecting portions that may damage neighbouring tissues.

WO 93/20771 describes a correction device, which, inter alia, intends to make the brace more flexible in order to facilitate the surgeon's work. This device comprises screws, holders and wires. The holders are attached by means of screws to suitable vertebrae. Between the holders there are arranged two parallel, spaced-apart wires. The wires are fixed in a first holder, passed through the next holder, clamped to a suitable degree and fixed in this holder while the spinal column is being straightened and compressed to a desirable extent, whereupon the wires are passed onto the next holder. The procedure is repeated until the intended portion of the spinal column has been straightened and compressed.

This device is certainly flexible during mounting, but unfortunately the flexibility is also to be found in the mounted construction. For instance, the device has no capability of absorbing forces acting in the longitudinal direction. Moreover, this device has poor torsional rigidity, which is a drawback when correcting scoliosis, since a spinal column suffering from scoliosis, as described above, is often twisted about its own longitudinal axis. A device for stabilising a straightened spinal column suffering from scoliosis should consequently be able to absorb torsional forces. The wire construction is also difficult to mount since the wires have no stability of their own. Therefore there is a risk that the surgeon tensions the wires too hard, which may result in overcorrection of the spinal column. Since the wires will necessarily have smaller cross-sectional dimensions than the above-mentioned rigid braces and besides will be subjected to considerable clamping forces in the holders, this device involves an increased risk of breaking. A broken wire would result in the neighbouring blood vessels being destroyed and the patient running the risk of bleeding to death.

U.S. Pat. No. 4,448,191 discloses a correction device for posterior fusion, comprising a resiliently pretensioned brace, which is intended to be arranged against the spinal column in such a manner that the spinal column is straightened by the pretensional force of the brace. As a result, the spinal column is forced to adjust to the brace. The correction thus takes place in one step by arranging the brace against the spinal column, and therefore the surgeon has no possibility of proceeding gradually along the spinal column. The device certainly accomplishes a straightening of the spinal column in the lateral direction, but at the same time makes the surgeon's work difficult by twisting and compressing the spinal column and will therefore be unsuitable for the correction of structural scoliosis. Besides, the device has projecting, sharp parts which in their mounted state may cause injuries to the patient.

U.S. Pat. No. 3,648,691 discloses a device for stabilising a spinal column by posterior fusion. Nor does this device permit compression of the spinal column since it has no adequate fixing means for this purpose. The ability of the device of absorbing torsional forces will also be insufficient for the correction of scoliosis.

SUMMARY OF THE INVENTION

One object of the present invention is to overcome the drawbacks of prior-art devices completely or at least to an essential extent, particularly to provide a device for correcting a deviating curvature of a spinal column, said device being easy to arrange on the spinal column and thus allowing shorter times of operation. In its mounted state, the device should wholly or partly stabilise the corrected spinal column.

A further object of the invention is to provide a device which can be fixedly anchored to the spinal column and which has little probability of breaking.

It is also an object to permit and facilitate compression of the spinal column when mounting the device.

One more object is to provide a device which easily allows further adjustment of the corrected spinal column.

It is also an object to provide a device which during operation is yieldable and which, in its mounted state, is able to absorb twisting forces.

A further object of the present invention is to provide a device which in its mounted state has little tendency to damage neighbouring blood vessels.

It is also an object to provide a method which wholly or partly overcomes the drawbacks of the prior-art methods of correcting and stabilising a curvature of a spinal column.

These and other objects which will appear from the following description have now been achieved by a device, a brace holder and a method of the type defined in appended claims 1, 9 and 14, respectively. The subclaims define preferred embodiments.

By using an inventive correction device, the operation times can be shortened to a considerable extent. The surgeon first mounts a number of brace holders on suitable vertebral bodies along the spinal column, whereupon the plate-shaped brace is mounted in the brace holders with a flat side facing the abutment surfaces of the brace holders on the vertebral bodies. Thanks to its plasticity, the plate-shaped brace can be easily and quickly bent to follow the extent of the uncorrected spinal column. The surgeon then locks the brace in a first brace holder and subsequently proceeds gradually along the spinal column, vertebra by vertebra, while twisting, displacing and compressing the spinal column to a corrected position and while gradually clamping and locking the brace in the brace holders.

Thanks to its plate shape, the brace is sufficiently flexible to facilitate mounting, but has at the same time an inherent rigidity which yields a risk, small in the context, of overcorrecting the spinal column. In its mounted state, the brace also has a considerable torsional rigidity and can absorb the retwisting force of the corrected spinal column.

The plate shape of the brace also permits such a form-fit locking in the brace holders that a postoperative twisting is rendered impossible.

The use of the plate-shaped brace in combination with the inventive brace holders results in the device in its mounted state being streamlined and not projecting from the spinal column.

BRIEF DESCRIPTION OF THE DRAWINGS

The invention and its advantages will be described in more detail below with reference to the accompanying drawings, which for the purpose of exemplification illustrate a presently preferred embodiment.

DESCRIPTION OF A PREFERRED EMBODIMENT

Figure 1:
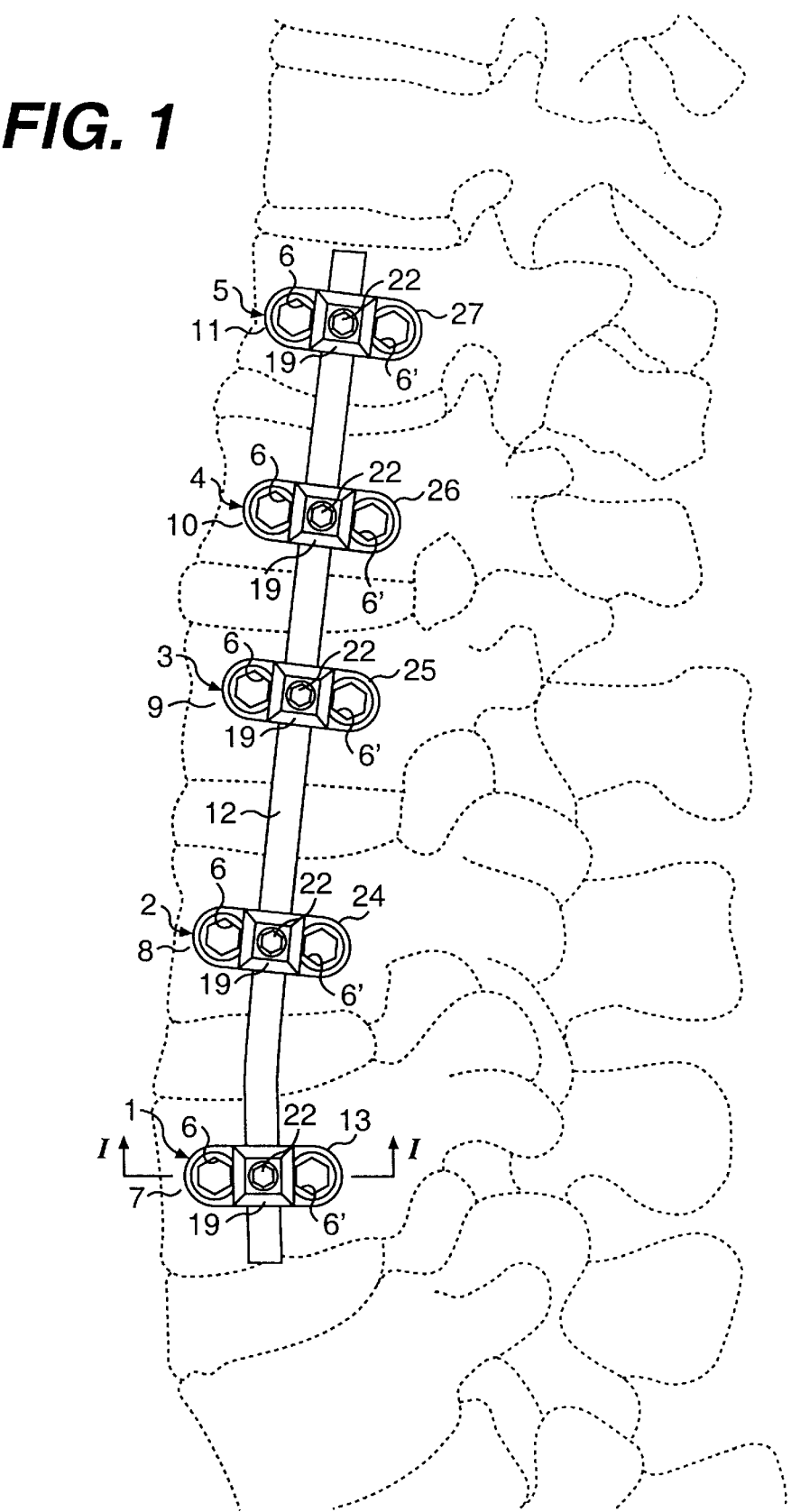
FIG. 1 is side view of an inventive device in mounted state, the device being mounted, for the sake of clearness, on a sound and, thus, uncorrected spinal column.

FIG. 1 shows the inventive device in mounted stated on a spinal column. In the embodiment shown, the device comprises five brace holders 1, 2, 3, 4, 5, two pedicel screws 6, 6' for securing the respective brace holders 1, 2, 3, 4, 5 on a vertebral body 7, 8, 9, 10, 11, and an elongate plate-shaped brace 12. Normally, a corresponding device is also arranged on the opposite side of the spinal column.

Figure 2:
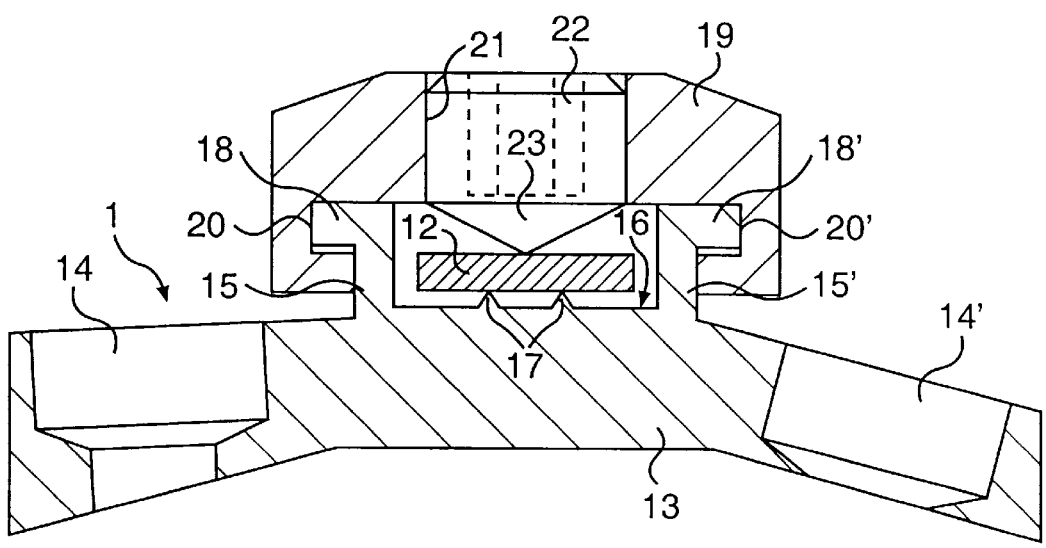
FIG. 2 is a cross-sectional view taken along line I—I in FIG. 1, the vertebral body and the pedicel screws not being shown for the sake of clearness.

The brace holder 1 has, as shown in FIG. 2, a frame comprising a long and narrow base plate 13, which in its end portions has a through mounting hole 14, 14' for receiving a pedicel screw 6, 6'. The underside of the base plate 13 is of a shape that essentially conforms with the outer surface of the vertebral body 7. On the upper side of the base plate 13, there are formed between the through mounting holes 14, 14' two flanges 15, 15' which project at right angles from the base plate 13 and which extend across the width of the base plate 13 and define, between themselves, a space and a flat supporting surface 16. In the supporting surface 16 there is formed a projecting locking element 17 in the form of two tips, whose size, however, is exaggerated in FIG. 2. The edge portions of the flanges 15, 15' facing away from the base plate 13 are formed with guiding flanges 18, 18', which extend from each other in a geometric plane essentially in parallel with the plane of the supporting surface 16.

The brace holder 1 further comprises a C-shaped cover plate 19. Two opposite grooves 20, 20' are formed on the inside of said C in such a manner that they can receive, in a form-fit manner, said guiding flanges 18, 18'. The cover plate 19 has a threaded through hole 21 for receiving a locking element in the form of a screw 22. The screw 22 has a pointed end portion 23 for engaging the brace 12. The opposite end portion of the screw 22 is formed with a hexagonal recess for engaging a suitable hexagon wrench. It will be appreciated that the design of the recess is not decisive of the invention. The brace holder 1 preferably is so designed that the screw 22 in its position locking the brace 12 is countersunk in the cover plate 19.

The pedicel screws 6, 6' are of conventional type and therefore not shown in more detail. They are designed to extend through the mounting holes 14, 14' and into the vertebral bodies 7, 8, 9, 10, 11.

The brace 12 is elongate, plate-shaped and preferably rectangular in cross-section. The brace 12 has a first and a second opposite flat side and two opposite edge faces. Thanks to its plate shape, the brace 12 can readily be deformed, i.e. bent, in a geometric plane extending perpendicularly to the flat sides of the brace 12. The brace 12 can only with great difficulty be deformed in the other geometric planes, where it has a great flexural resistance thanks to its thickness. The brace is preferably made of stainless steel, but other metal materials are also conceivable, e.g. titanium. The width of the brace is about 4–10 mm, preferably about 5–8 mm, and its thickness is about 1–3 mm, preferably about 1.5–2 mm.

The surgical procedure for mounting the correcting device will be described in more detail below.

First, the surgeon uncovers a portion of the spinal column from the patient's trunk side. Normally four to six vertebral bodies and discs are uncovered from the convex side of the scoliosis, whereupon a resection of the discs is carried out, in which the major part of the discs is removed. Subsequently, a first base plate 13 is mounted on an uncovered vertebral body 7 and is attached by screwing two pedicel screws 6, 6' into the spongeous bone of the vertebral body 7. The surgeon then fastens further base plates on suitable vertebral bodies 8, 9, 10, 11 along the extent of the not yet corrected spinal column. A plate-shaped brace 12 is then arranged on the flat supporting surface 16 of the first base plate 13, whereupon the cover plate 19 is attached to the base plate 13 by slidingly moving the grooves 20, 20' over the guiding flanges 18, 18', and screwing a locking element 22 into the holes 21 of the cover plate 19. Then the brace 12 is advanced and arranged on the supporting surface of a subsequent second base plate 24, whereupon a cover plate 19 and a locking element 22 are mounted on the second base plate. This procedure is repeated until the farther base plate 27 has been reached and the brace 12 consequently extends along the portion of the spinal column that is to be corrected. Subsequently all locking elements 22 are clamped such that the tips 23 abut against and engage with the flat side of the brace 12 facing away from the vertebral bodies 7, 8, 9, 10, 11. It will be appreciated that the pointed locking element 17 in the supporting surface 16 engages with the flat side of the brace 12 facing the vertebral bodies 7, 8, 9, 10, 11 and contributes to the locking of the brace 12 in the respective brace holders 1, 2, 3, 4, 5. It is worth noticing that in the initial unlocked mounting in the brace holders 1, 2, 3, 4, 5, the brace 12 is deformed to take a shape that essentially follows the extent of the not yet corrected spinal column.

The surgeon then releases the locking element 22 of the second brace holder 2 and compresses the spinal column portion between the first and the second holder 1, 2 by means of a special compression instrument (not shown). During this step, the twisting and lateral displacement, caused by scoliosis, of the spinal column portion is corrected. During compression, the locking element 22 of the second brace holder 2 is clamped against the brace 12, which thus is fixed in its position. The step is then repeated, brace holder by brace holder, along the spinal column until the correction is completed.

The brace holder 1 is arranged on the vertebral body 7 for supporting the brace 12 in such a manner that one flat side of the brace 12 faces the abutment surface of the brace holder 1 on the vertebral body 7. Thus, the brace 12 is deformable during mounting exclusively in a geometric plane that is essentially parallel with the misplaced plane of the spinal column, i.e. the plane in which the curvature extends. In the correction of scoliosis, the misplaced plane is substantially perpendicular to the sagittal plane of the spinal column, and in the correction of kyphosis, essentially in parallel with said sagittal plane. Thanks to the plate shape, the surgeon can relatively easily, without the aid of special instruments, deform the brace 12 to extend along the curvature of the spinal column. The metallic brace 12 thus applies to the spinal column a certain spring-back force which strives to straighten the spinal column. The resilience of the brace 12 in the misplaced plane of the spinal column also facilitates the surgeon's work to such an extent that, during the gradual correction, he can easily adapt the extent of the brace 12 to the corrected spinal column.

The brace 12, of course, is differently deformable depending on its thickness. Thin braces having a thickness of about 1–1.5 mm have great flexibility. These braces should, however, be supplemented with a conventional posterior correction device to give the corrected spinal column sufficient stability. Such a posterior correction device can, however, be mounted relatively quickly since the spinal column is already corrected by means of the inventive device.

Thicker braces having a thickness of about 1.5–3 mm give the corrected spinal column greater stability and can in some cases be used on their own, i.e. without a posterior correction device. These braces are still sufficiently deformable to facilitate the surgeon's correction work.

The use of a plate-shaped brace 12 together with the suitably designed brace holders 1, 2, 3, 4, 5 results in considerably shortened operation times. By conventional technique, the operation time in an anterior fusion is about 4–5.5 h, of which about 2–2.5 h are necessary for the actual correction and stabilisation of the spinal column. Clinical experiments have shown that the use of a device according to the invention can shorten the operation time in a front fusion to about 3–4.5 h by shortening the work with the stabilisation and correction of the spinal column by about 1–1.5 h.

As is evident from the above description, the device is intended for anterior fusions, more specifically for mounting on the vertebral bodies 7, 8, 9, 10, 11 of the spinal column. The use of pedicel screws 6, 6' results in a very reliable attachment of the brace holders 1, 2, 3, 4, 5 on the vertebral bodies 7, 8, 9, 10, 11.

Thanks to the plate shape of the brace, the device has a good torsional rigidity in its mounted state in spite of its resilience during mounting, and can therefore absorb the retwisting force of the corrected spinal column. The device is preferably used in a pair, i.e. a further device is mounted on the opposite side of the spinal column.

A great advantage of the device is that it can be mounted very close to the spinal column, which reduces the risk that projecting parts damage neighbouring blood vessels and tissues when the patient begins to move after the operation.

The design of the brace holder 1 with a detachable cover plate 19 facilitates the correction since the surgeon can bend the brace 12 into direct abutment against the supporting surface 16 and then mount the cover plate 19 for retaining the brace 12 against the action of its spring-back force. Alternatively it is conceivable to integrate the brace holder 1 with a through duct (not shown) receiving the brace. In this case, however, the brace 12 must be simultaneously bent and slidingly displaced during mounting, which will probably make the work somewhat more difficult.

It is preferable that the distance between the projecting flanges 15, 15' of the brace holder 1 exceeds the width of the brace 12 by preferably at least 1 mm. As a result, the mounting of the brace 12 against the supporting surface 16 of the brace holder 1 is facilitated.

The brace holder 1 is so designed that the brace 12 cannot twist in the holder 1 after operation. In the locked state, one flat side of the brace 12 therefore abuts against the flat supporting surface 16. Besides, the distance between the supporting surface 16 and the cover plate 19 preferably is smaller than the width of the brace 12.

It will be appreciated that the device can easily be further adjusted by the surgeon loosening the brace 12 adjacent the second brace holder 2 and again proceeding along the spinal column as described above.

What is claimed is:

1. A device for correcting and stabilizing a deviating curvature of a spinal column by anterior fusion, comprising:
    at least two brace supporting holders each having a surface to contact with an associated vertebral body in the spinal column;
    securing means for securing the respective brace holders on said vertebral body; and
    an elongate brace adapted to extend through and between said brace holders and to be locked thereto, said brace being rectangular in cross section, having flat sides of a width in a range of about 5 to 8 mm, a thickness in a range of about 1 to 3 mm, and being made of stainless steel or titanium to be manually deformable in a geometric plane extending perpendicularly to the flat sides of the brace;
    wherein each of the brace supporting holders supports the brace in such a manner that a first flat large side of the brace faces the contact surface of the brace holder on said vertebral body, whereby the brace is deformable only in said geometric plane during mounting without being locked to the brace holders, and during correction, to follow the curvature of the spinal column.

2. The device of claim 1, wherein the brace has a torsional rigidity sufficient to withstand a re-twisting moment of the corrected spinal column.

3. The device of either of claims 1 or 2, wherein the brace has a thickness in a range of about 1.5 to 2 mm.

4. The device of claim 3, wherein the securing means comprises at least one screw extendable through a recess in the respective brace holders.

5. The device of claim 3, wherein the brace holder comprises a frame for receiving the brace, and a first locking element threadable into a recess in the frame and having one end portion to contact and lock the brace relative to the frame, the frame comprising a base plate with the surface for contacting the respective vertebral bodies and for receiving the brace, and a detachable cover plate for engaging the base plate, the recess being formed in the cover plate.

6. The brace holder of claim 5, wherein said end portion of the first locking element is adapted to engage a second large flat side of the brace.

7. The brace holder of claim 5, wherein the base plate has a flat brace supporting surface for receiving the brace.

8. The brace holder of claim 5, wherein the base plate has a brace supporting surface with projecting second locking elements.

9. The brace holder of claim 5, wherein the first locking element is of a length such that an end portion opposite from said one end portion is countersunk in the recess in the cover plate when the brace is locked.

10. A method of correcting and stabilizing a curvature of the spinal column, comprising the steps of:
    a) uncovering a portion of the spinal column;
    b) arranging at least two brace holders on uncovered vertebral bodies along the portion of the spinal column that is to be corrected;
    c) arranging a plate-shaped brace to extend through said brace holders, such that the brace is deformed to generally follow the curvature of the spinal column;
    d) locking the brace in at least a first brace holder;
    e) correcting a spinal column portion located between the first brace holder and a second neighboring unlocked brace holder, and thereafter locking the brace in the second brace holder; and
    f) repeating step e) between neighboring brace holders along the spinal column until the correction has been completed.

11. The method of claim 10, wherein step d) comprises locking the brace in all brace holders, and wherein step e) comprises releasing the brace in the second neighboring brace holder, correcting the spinal column portion between the first and second brace holders, and locking the brace in the second brace holder.

* * * * *